United States Patent
Misawa et al.

(10) Patent No.: US 12,158,579 B2
(45) Date of Patent: Dec. 3, 2024

(54) HEAD-UP DISPLAY APPARATUS

(71) Applicant: MAXELL, LTD., Kyoto (JP)

(72) Inventors: Akio Misawa, Kyoto (JP); Yuji Fujita, Kyoto (JP)

(73) Assignee: MAXELL, LTD., Kyoto (JP)

(*) Notice: Subject to any disclaimer, the term of this patent is extended or adjusted under 35 U.S.C. 154(b) by 169 days.

(21) Appl. No.: 17/423,952

(22) PCT Filed: Nov. 22, 2019

(86) PCT No.: PCT/JP2019/045869
§ 371 (c)(1),
(2) Date: Jul. 19, 2021

(87) PCT Pub. No.: WO2020/152970
PCT Pub. Date: Jul. 30, 2020

(65) Prior Publication Data
US 2022/0091415 A1 Mar. 24, 2022

(30) Foreign Application Priority Data
Jan. 25, 2019 (JP) .................... 2019-010985

(51) Int. Cl.
*G09G 3/02* (2006.01)
*A61B 5/00* (2006.01)
(Continued)

(52) U.S. Cl.
CPC .......... *G02B 27/0101* (2013.01); *A61B 5/163* (2017.08); *A61B 5/6821* (2013.01);
(Continued)

(58) Field of Classification Search
CPC .................................................... G02B 27/01
See application file for complete search history.

(56) References Cited

U.S. PATENT DOCUMENTS 5,734,357 A * 3/1998 Matsumoto ........ G02B 27/0149
359/632
2006/0103590 A1* 5/2006 Divon ...................... G08B 5/36
455/344
(Continued)

FOREIGN PATENT DOCUMENTS

JP 03-42337 A 2/1991
JP 06-247184 A 9/1994
(Continued)

OTHER PUBLICATIONS

International Search Report of PCT/JP2019/045869 dated Feb. 4, 2020.

*Primary Examiner* — Nan-Ying Yang
(74) *Attorney, Agent, or Firm* — Mattingly & Malur, PC

(57) ABSTRACT

A head-up display apparatus configured to project an image on a windshield to display a virtual image to a driver includes an image display unit including a light source and a display element and configured to form the image. A display device is configured to project and reflect image light onto the windshield to display the virtual image in front of the windshield. A driver's viewpoint detector is configured to detect a viewpoint of the driver; and a movement mechanism is configured to move a position of the virtual image based on information of the viewpoint of the driver detected by the driver's viewpoint detector. The driver's viewpoint detector detects the viewpoint of the driver by irradiating the face of the driver with the interior light or light of the light source of the image display unit as illumination light at night.

11 Claims, 13 Drawing Sheets

(51) Int. Cl.
*A61B 5/16* (2006.01)
*B60K 35/00* (2006.01)
*G02B 27/00* (2006.01)
*G02B 27/01* (2006.01)
*G06F 3/01* (2006.01)
*B60K 35/23* (2024.01)
*B60K 35/60* (2024.01)

(52) U.S. Cl.
CPC .......... *B60K 35/00* (2013.01); *G02B 27/0093* (2013.01); *B60K 35/23* (2024.01); *B60K 35/60* (2024.01); *B60K 2360/785* (2024.01)

(56) References Cited

U.S. PATENT DOCUMENTS

| | | | |
|---|---|---|---|
| 2009/0256904 A1* | 10/2009 | Krill | H04N 13/344 |
| | | | 348/47 |
| 2012/0134547 A1 | 5/2012 | Jung | |
| 2014/0354514 A1* | 12/2014 | Aronsson | G06T 19/006 |
| | | | 345/7 |
| 2016/0148065 A1* | 5/2016 | Lee | H04N 23/611 |
| | | | 348/78 |
| 2017/0115485 A1 | 4/2017 | Saito et al. | |
| 2017/0160545 A1 | 6/2017 | Sugiyama et al. | |
| 2017/0315623 A1* | 11/2017 | Yao | G06F 3/021 |
| 2020/0290458 A1 | 9/2020 | Sunaga et al. | |
| 2021/0112647 A1* | 4/2021 | Coleman | H05B 45/12 |

FOREIGN PATENT DOCUMENTS

| | | |
|---|---|---|
| JP | 2006219000 A | 8/2006 |
| JP | 2009043003 A | 2/2009 |
| JP | 2010125910 A | 6/2010 |
| JP | 2011152883 A | 8/2011 |
| JP | 2012113687 A | 6/2012 |
| JP | 2014199385 A | 10/2014 |
| JP | 2015219631 A | 12/2015 |
| JP | 2016014861 A | 1/2016 |
| JP | 2016068577 A | 5/2016 |
| JP | 2016210259 A | 12/2016 |
| JP | 2019101323 A | 6/2019 |

* cited by examiner

FIG. 3
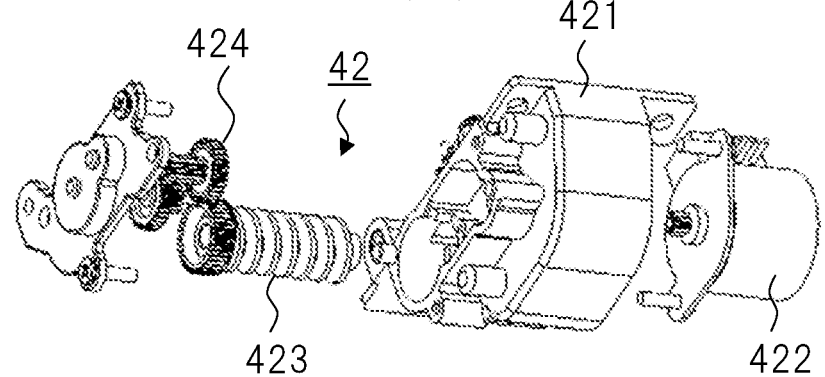
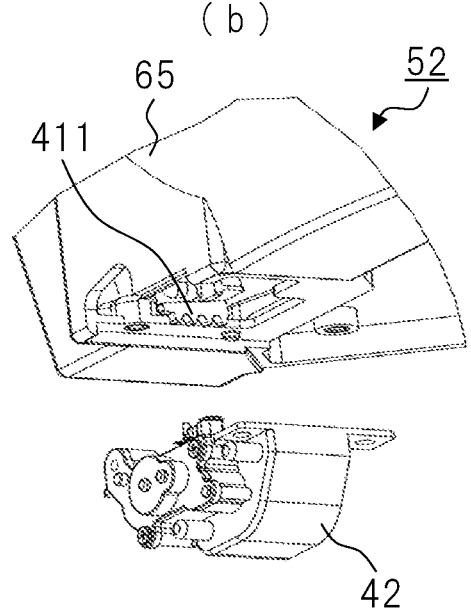
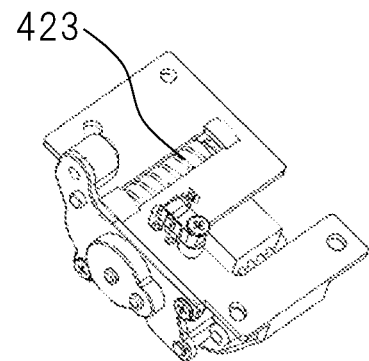

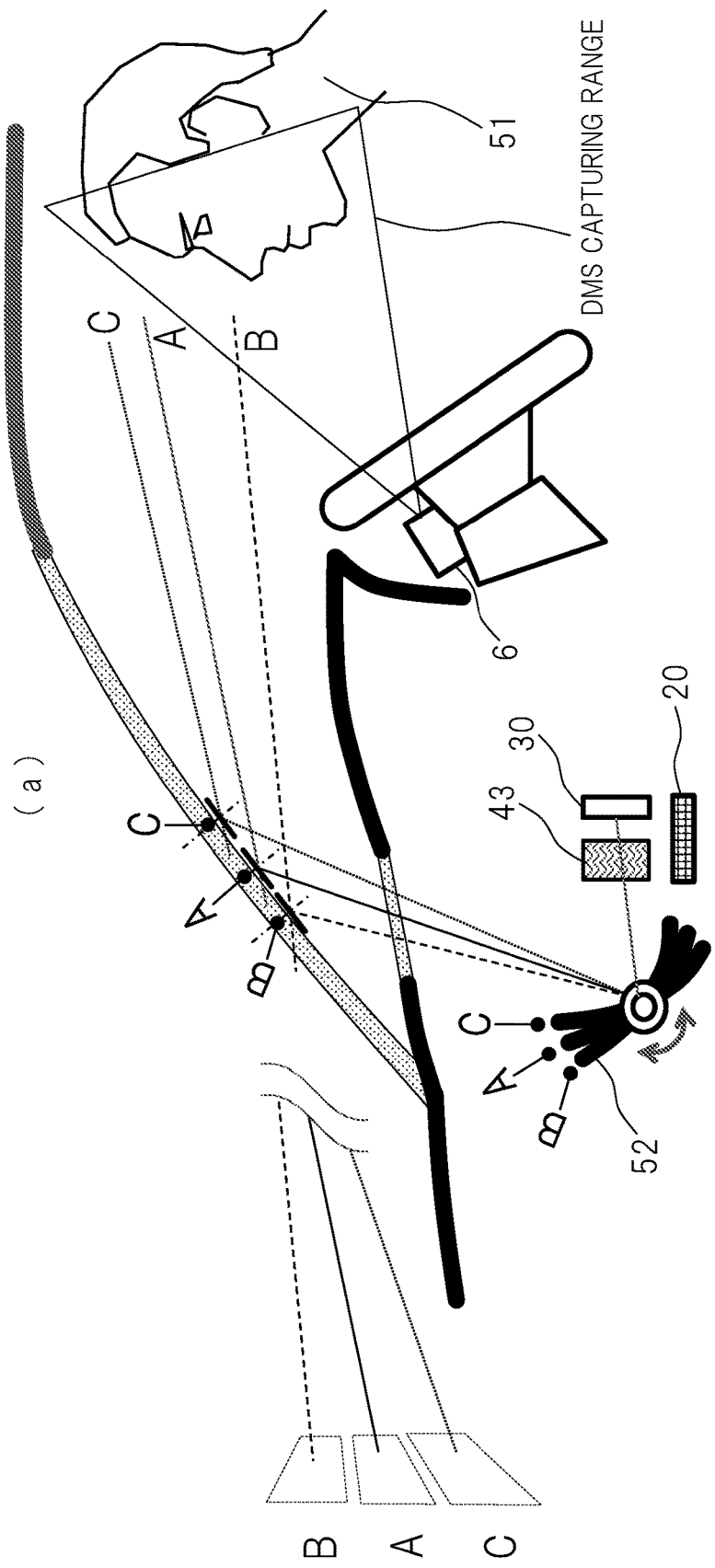
FIG. 13

HEAD-UP DISPLAY APPARATUS

TECHNICAL FIELD

The present invention relates to a technique of a head-up display apparatus, and more particularly to a technique effectively applied to a head-up display apparatus configured to project an image on transparent glass or the like.

BACKGROUND ART

For example, in a vehicle such as an automobile, information such as a vehicle speed and an engine speed is usually displayed on an instrument panel (meter panel) in a dashboard. In addition, a screen for a car navigation or the like is incorporated in a dashboard or displayed on a display installed on the dashboard. Since it is necessary for a driver to greatly move a line of sight when the driver visually recognizes the information, a head-up display (Head-Up Display, hereinafter referred to also as "HUD") apparatus that projects and displays information such as a vehicle speed and information such as an instruction related to a car navigation on a windshield (windscreen) or the like is known as a technique for reducing the movement amount of the line of sight.

As a technique related to such a HUD, for example, Patent Documents 1 to 3 below disclose techniques in which a HUD and a viewpoint detection camera are combined.

In addition, Patent Document 4 below describes a technique for changing a display position of a projection image which is a virtual image so as to correspond to a viewpoint position of an observer with a simple configuration.

RELATED ART DOCUMENTS

Patent Documents

Patent Document 1: Japanese Unexamined Patent Application Publication No. 2016-068577
Patent Document 2: Japanese Unexamined Patent Application Publication No. 2015-219631
Patent Document 3: Japanese Unexamined Patent Application Publication No. 2014-199385
Patent Document 4: Japanese Unexamined Patent Application Publication No. 2016-014861

SUMMARY OF THE INVENTION

Problems to be Solved by the Invention

In the related art described above, in particular, the related art described in Patent Document 4 describes that, in order to efficiently direct image light to an observer, a viewpoint position of a driver is detected by a viewpoint position detector such as an infrared camera, and a display position of a projection image is moved in accordance with the detected viewpoint position. However, in that case, in addition to a normal driver monitoring system for supporting safe driving by detecting an attitude, a line of sight, and the like of a driver during driving, an infrared generator, an infrared camera, and the like need to be installed in a small space near the driver's seat as the viewpoint position detector, which leads to an increase in cost of the apparatus, and is not necessarily optimal.

Therefore, an object of the present invention is to provide a practical and economical head-up display apparatus capable of detecting a viewpoint position of a driver who is an observer of a virtual projection image by a viewpoint detector that operates with normal visible light to confirm a position of the driver by using an existing interior light or a light source of HUD apparatus without using a dedicated light source such as infrared light, and capable of suitably controlling the virtual projection image without unnecessarily generating white light by the HUD apparatus.

Means for Solving the Problems

A typical embodiment of the present invention will be briefly described below. A head-up display apparatus configured to project an image on a windshield of a transportation to display a virtual image based on the image to a driver includes: an image display unit including a light source and a display element and configured to form the image; a display device configured to project and reflect image light emitted from the image display unit onto the windshield to display the virtual image in front of the transportation; a driver's viewpoint detector configured to detect a viewpoint of the driver; and a movement mechanism configured to move a position of the virtual image projected by the image display unit based on information of the viewpoint of the driver detected by the driver's viewpoint detector. In the head-up display apparatus, the transportation is provided with an interior light device near a driver's seat, and the driver's viewpoint detector detects the viewpoint of the driver by irradiating a face of the driver with light of the interior light device or light of the light source of the image display unit as illumination light under a predetermined environment of the transportation.

Effect of the Invention

An effect achieved by a typical embodiment of the present invention will be briefly described as follows. Namely, according to the typical embodiment of the present invention, it is possible to provide a head-up display apparatus which is excellent in practical use and economical efficiency and capable of reliably confirming a viewpoint position of a driver and suitably controlling a virtual projection image even in an environment where sufficient visible light cannot be obtained such as at night.

BRIEF DESCRIPTIONS OF THE DRAWINGS

FIG. 1 is a diagram showing an example of an overall configuration of a head-up display apparatus according to an embodiment of the present invention;
FIG. 2 is a diagram showing a detailed configuration of an mounting form of the head-up display apparatus;
FIG. 3 is a diagram including a development diagram, an assembly diagram, and an overall diagram showing an example of a configuration of a mirror driver of the head-up display apparatus;
FIG. 4 is a diagram showing an example of an operation of the mirror driver of the head-up display apparatus;
FIG. 5 is a block diagram showing an example of a control system in the head-up display apparatus;
FIG. 6 is a block diagram showing an example of a vehicle information acquisition unit constituting the head-up display apparatus;
FIG. 7 is a block diagram showing an example of a configuration of a viewpoint detector of the head-up display apparatus;

FIG. 13 is an explanatory diagram for an operation principle of the detection of a viewpoint position of a driver.

DETAILED DESCRIPTION OF PREFERRED EMBODIMENTS

Figure 1:
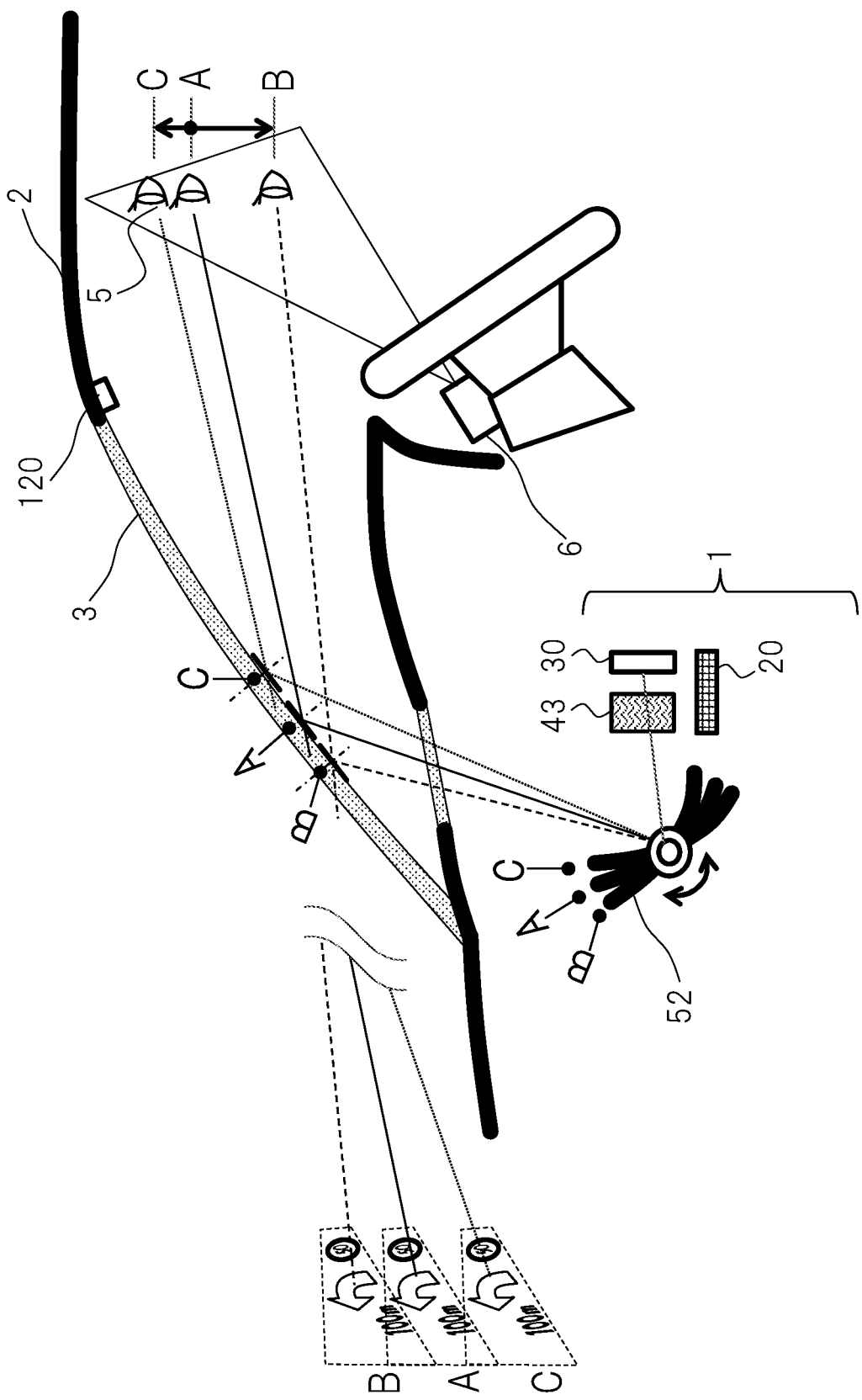

Hereinafter, embodiments of the present invention will be described in detail with reference to the drawings. In all the drawings for describing the embodiments, the same components are denoted by the same reference numerals in principle, and the repetitive description thereof will be omitted. On the other hand, a component which has been described with a reference numeral being attached in a certain drawing may be referred to with the same reference numeral being attached in the description of other drawings though not shown again. Furthermore, in each of the following embodiments, a case where a head-up display (HUD) apparatus is installed in a vehicle such as an automobile will be described as an example, but the present invention is also applicable to other transportations such as a train and an aircraft.

FIG. 1 is a diagram showing an outline of an example of a configuration of a head-up display (HUD) apparatus according to an embodiment of the present invention. A HUD apparatus 1 is configured to display a desired projection image at a corresponding viewpoint position of an observer (driver) by passing light of an image display device 30, which is arranged in a housing (not shown) and modulates light from a light source to project the modulated light, through a necessary optical element 43 and further reflecting it by a concave mirror 52, and then projecting the light on a windshield 3 of a vehicle 2 to be incident on a viewpoint 5 of the observer. Note that, in this figure, rotation positions of the concave mirror 52, projection positions of the projection image on the windshield 3 (inner surface side), and virtual images displayed by the projection corresponding to different positions of the viewpoint 5 of the observers (drivers) are indicated by A, B, and C, respectively.

Further, a controller 20 configured to control the HUD apparatus 1 including the image display device 30 and the concave mirror 52 and a viewpoint detector 6 such as a driver monitoring system (DMS) that includes an in-vehicle camera for monitoring an attitude including a viewpoint of a driver are shown in this figure. In addition, a reference numeral 120 in the figure indicates an existing interior light that is installed near a driver's seat, more specifically, on a ceiling above the driver's seat, is interlocked with opening and closing of a door of the vehicle, and can be turned on/off as needed by the driver. As will be apparent from the following description, the interior light 120 also has a role as a light source for detecting the viewpoint position of the driver while being turned on.

Here, a projection target member is not limited to the windshield 3, and may be another member such as a combiner as long as an image can be projected on the member. Furthermore, the image display device 30 is configured of, for example, a projector having a backlight (light source) 31 (FIG. 2), a liquid crystal display (LCD), or the like. The image display device 30 may be a self-luminous vacuum fluorescent display (VFD) or the like or may have a configuration to display an image on a screen by a projection device. Such a screen may be configured of, for example, a microlens array in which microlenses are two-dimensionally arranged.

The concave mirror 52 is configured of, for example, a free-form surface mirror or a mirror having a shape asymmetrical with respect to an optical axis. More specifically, in order to reduce distortion of a virtual image, for example, in an upper region of the concave mirror 52 (that is, a region having a relatively short distance to the driver's viewpoint 5 because a light beam reflected here is reflected at a lower portion of the windshield 3), a radius of curvature is relatively decreased such that a magnification factor increases. On the other hand, in a lower region of the concave mirror 52 (that is, a region having a relatively long distance to the driver's viewpoint 5 because a light beam reflected here is reflected at an upper portion of the windshield 3), the radius of curvature is relatively increased such that the magnification factor decreases. It is also possible to reduce the generated distortion itself by correcting a difference in image magnification by arranging the image display device 30 to be inclined with respect to an optical axis of the concave mirror 52.

The driver sees an image projected on the windshield 3 from the viewpoint 5 to visually recognize the image as a virtual image in front of the windshield 3 through the transparent windshield 3. At that time, by adjusting an angle of the concave mirror 52, a position where the image is projected on the windshield 3 can be adjusted, so that a display position of the virtual image can be adjusted in a vertical direction with respect to the position of the viewpoint 5. Note that the content to be displayed as the virtual image is not particularly limited, and for example, vehicle information, navigation information, an image of a forward landscape captured by a camera (monitoring camera, around viewer, or the like (not shown)), and the like can be displayed as appropriate.

Further, a reference numeral 6 donates a viewpoint detector that is attached to a part of a steering wheel and detects a viewpoint and an attitude of the driver under normal visible light or the like. However, the viewpoint detector 6 such as a driver monitoring system (DMS) including an in-vehicle camera is not necessarily attached to a part of a steering wheel as described above, and may be attached to, for example, a part of a dashboard or a part of the windshield 3 as long as the driver's viewpoint and the like can be detected.

Figure 2:
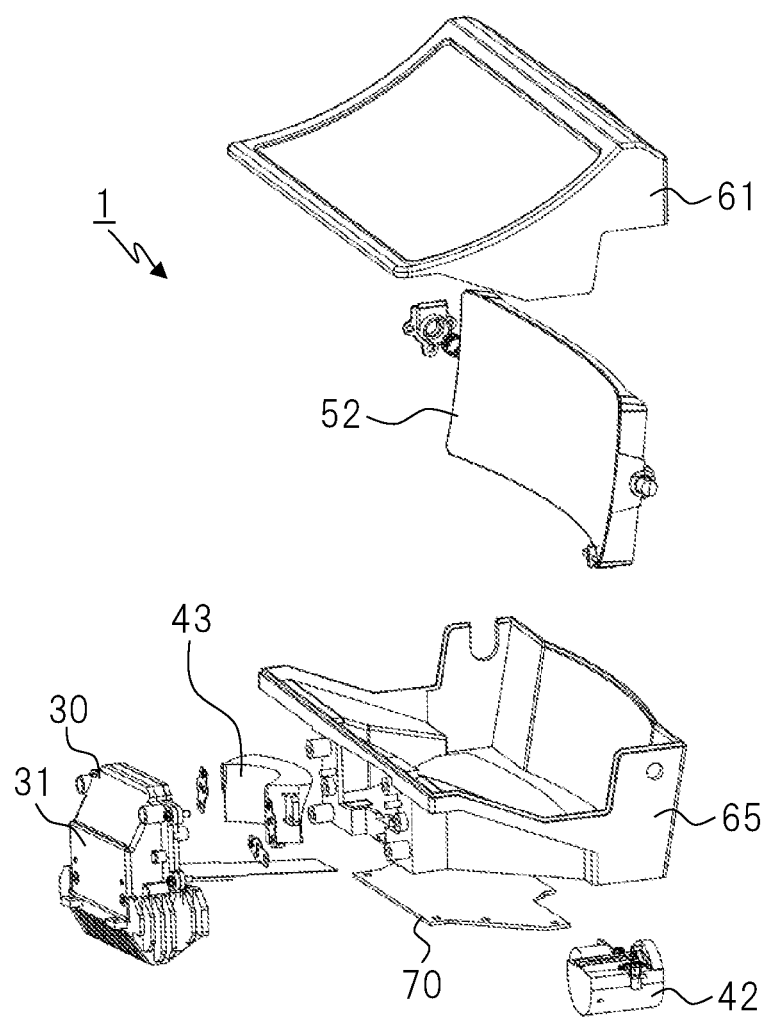

FIG. 2 shows an example of a detailed structure of the HUD apparatus 1. Here, the housing is denoted by reference numerals 61 and 65, and the HUD apparatus 1 is configured by combining the image display device 30 and the concave mirror 52 with each other. Furthermore, a distortion correction lens or the like as a necessary optical element is indicated by a reference numeral 43.

In this example, as is clear from the figure, the concave mirror 52 is arranged inside the housings 61 and 65 so as to be rotatable within a slight angle range by a pair of shafts formed on side surfaces. Furthermore, a main board 70 on which a controller and the like are mounted and a mirror driver 42 composed of moving mechanisms such as a motor, a worm gear, and a wheel are attached to a bottom portion of the lower housing 65 by a fixing mechanism such as screws. Namely, the mirror driver can change an inclination angle of the concave mirror 52 described above within a slight angle range.

FIG. 3 is a diagram showing an outline of a mounting example of the mirror driver 42 for changing the inclination angle of the concave mirror 52. Here, as also shown in FIG. 3(a), the mirror driver 42 includes, in a case 421, at least an electric motor 422 whose rotation speed can be controlled in a wide range from high-speed rotation to low-speed rotation, a worm gear 423, and a plurality of gears 424 combined between an output shaft of the motor and the worm gear. As also shown in FIG. 3(b), the mirror driver 42 is attached at an outer peripheral portion of the housing, more specifically, at a lower end portion of the optical component holding exterior case 65 described above such that the worm gear 423 meshes with a worm wheel 411 formed at a lower end portion of the concave mirror 52 via a part of a cutout portion. FIG. 3(c) is a diagram as viewed from a joint side.

Figure 4:
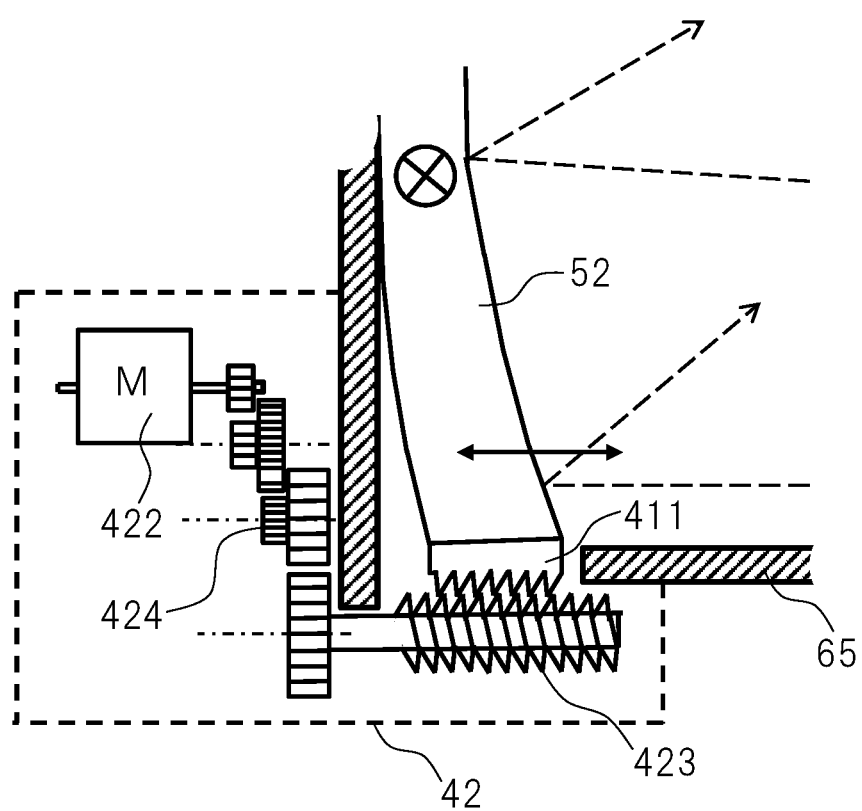

Note that, in the configuration of the mirror driver 42 described above, as also shown in FIG. 4, the rotation of the electric motor 422 whose rotation can be controlled in a wide range from low speed to high speed is converted into a desired rotation speed/driving force via the plurality of gears 424 and transmitted to the worm gear 423, and further, the worm wheel 411 formed at the lower end portion of the concave mirror 52 is moved in a front-rear direction (see the arrow in FIG. 4) by rotating the worm gear 423 about a rotation axis, so that the concave mirror 52 can be adjusted to a desired inclination angle. Note that, in this figure, the plurality of gears 424 are shown at intervals for ease of illustration, but it is obvious for those skilled in the art that these gears are meshed with each other in practice.

Figure 5:
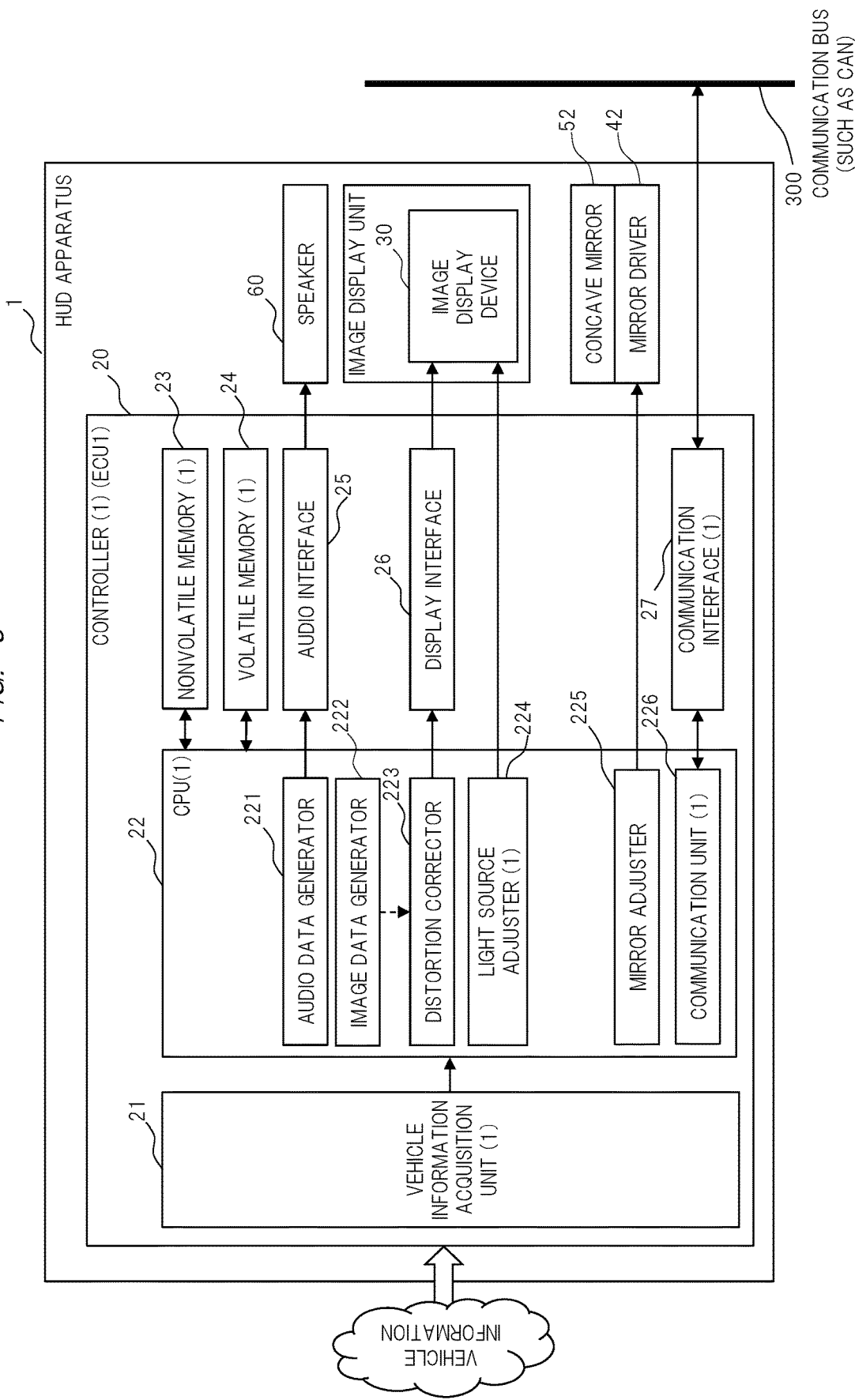

Subsequently, the controller (1) (ECU1) 20 of the HUD apparatus 1 has a function of controlling an operation of the HUD apparatus 1. As shown in FIG. 5, for example, the controller (1) (ECU1) 20 includes a vehicle information acquisition unit (1) 21, a CPU (Central Processing Unit) (1) 22, a nonvolatile memory (1) 23, a volatile memory (1) 24, an audio interface 25, a display interface 26, a communication interface (1) 27, and the like. Note that, in the figure, functions of the CPU (1) 22 realized by executing the software stored in the nonvolatile memory (1) 23 by the volatile memory (1) 24 are shown by blocks of an audio data generator 221, an image data generator 222, a distortion corrector 223, a light source adjuster (1) 224, a mirror adjuster 225, and a communication unit (1) 226. Data generated by the audio data generator 221 is output to a speaker 60 via the audio interface 25, and data generated by the image data generator 222 is output to the image display device 30 of the image display unit via the display interface 26 after distortion thereof is corrected by the distortion corrector 223. Note that data from the light source adjuster (1) 224 is directly output to the image display device 30. Also, data from the mirror adjuster 225 is output to the mirror driver 42.

On the other hand, various signals from a communication bus (such as CAN) 300 provided in the vehicle 2 are input to the communication unit (1) 226 of the CPU (1) 22 via the communication interface (1) 27. Namely, as also shown in this figure, the controller (1) (ECU1) 20 drives the image display device 30 to form an image to be displayed as a virtual image based on vehicle information or the like acquired from the vehicle information acquisition unit (1) 21, and reflects the image by the concave mirror 52 (FIG. 1) controlled by the mirror driver 42 to project the image on the windshield 3 (FIG. 1). At the same time, the inclination angle of the concave mirror 52 is controlled by the above-described mirror driver 42.

Figure 6:
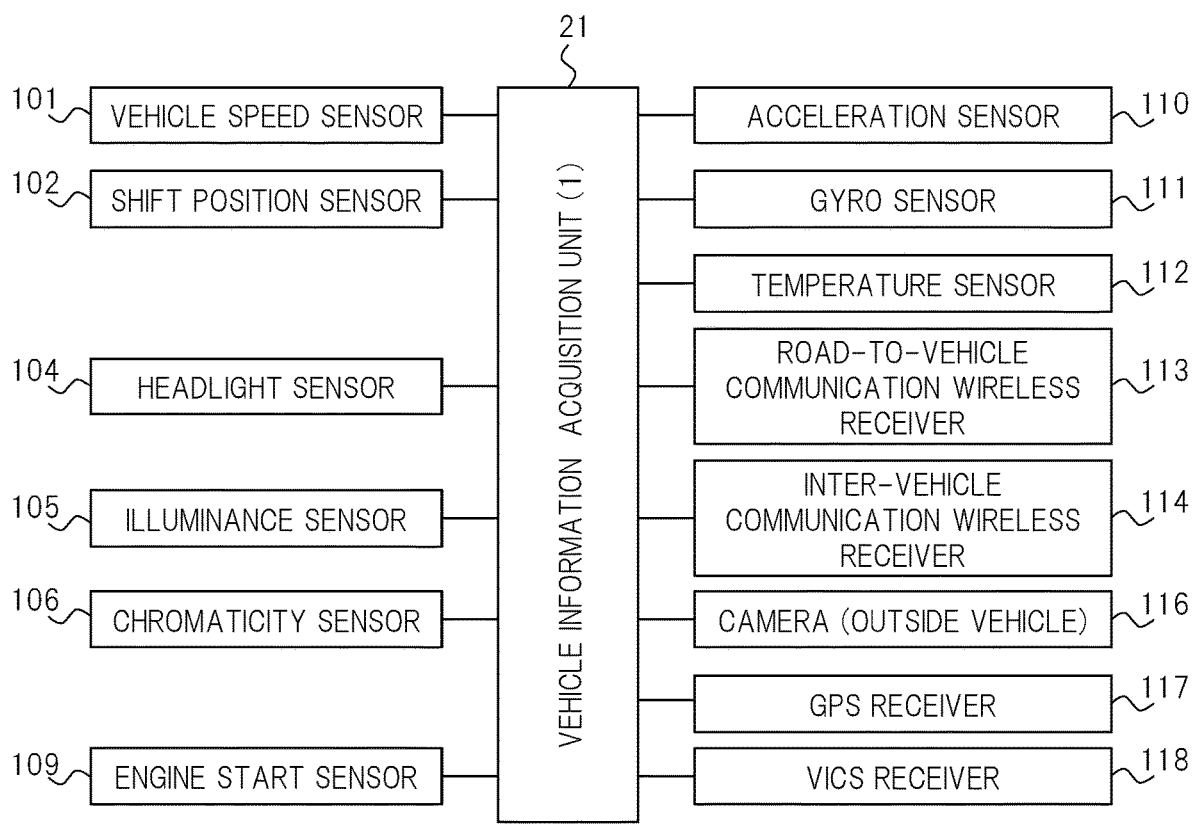

As also shown in FIG. 6, for example, the vehicle information acquisition unit (1) 21 includes a vehicle speed sensor 101, a shift position sensor 102, a headlight sensor 104, an illuminance sensor 105, a chromaticity sensor 106, an engine start sensor 109, an acceleration sensor 110, a gyro sensor 111, and a temperature sensor 112, and further includes a road-to-vehicle communication wireless receiver 113, an inter-vehicle communication wireless receiver 114, a camera (outside vehicle) 116, a GPS receiver 117, a VICS receiver 118, and the like. However, all of these devices are not necessarily provided, or other types of devices may be further provided. In addition, vehicle information that can be acquired by these devices can be used as appropriate. As described above, a HUD control system is composed of information acquisition devices such as various sensors installed in various parts of the vehicle 2 (FIG. 2), and can acquire and output vehicle information by detecting various events occurring in the vehicle 2 and detecting and acquiring values of various parameters related to traveling status at predetermined intervals.

The vehicle speed sensor 101 is provided to grasp vehicle speed, and the engine start sensor 109 is provided to grasp start of an engine and the system is started when the engine is started. The camera (outside vehicle) is provided to detect a vehicle, a person, and an obstacle ahead.

Figure 7:
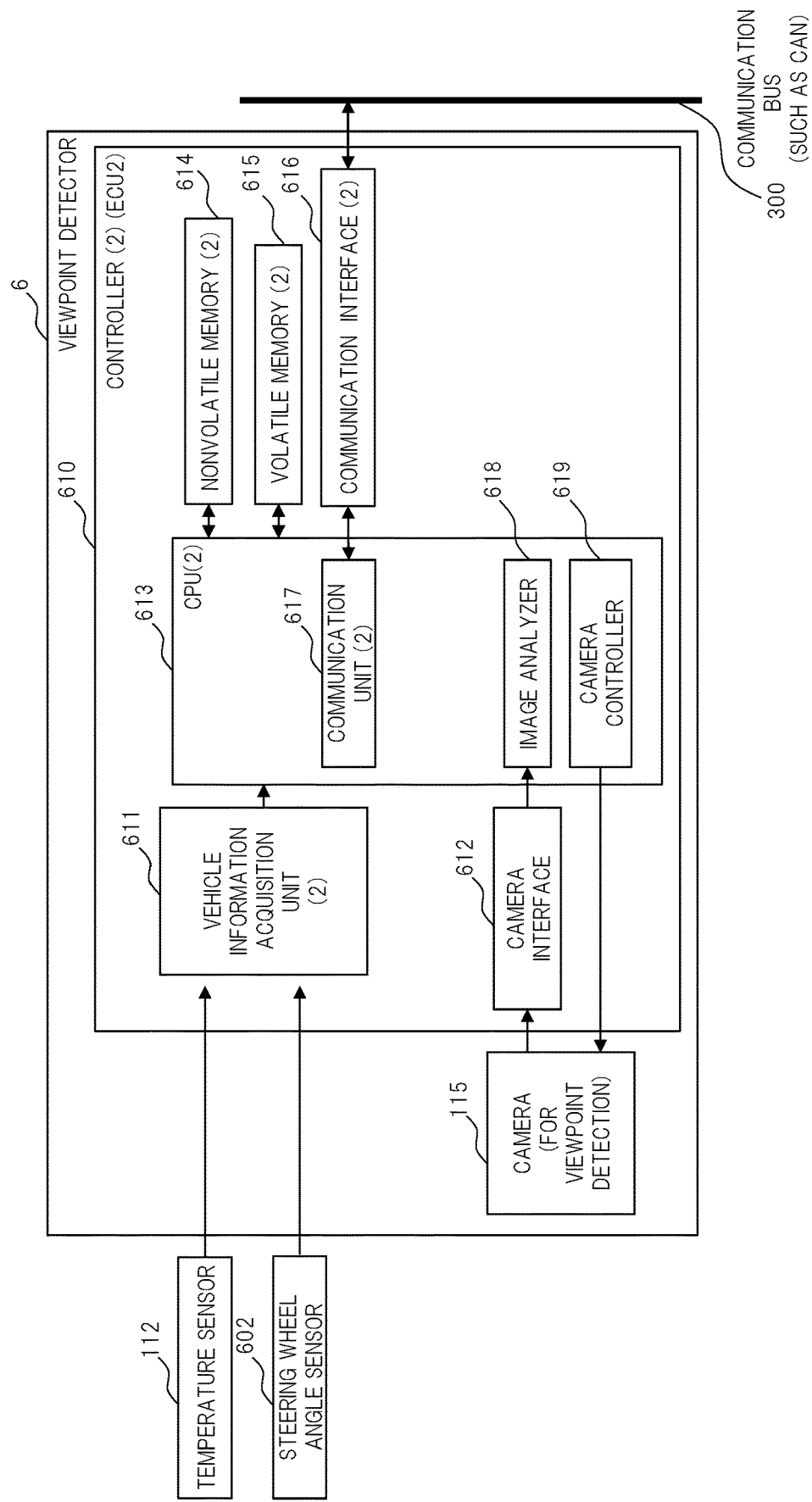

FIG. 7 shows an example of a configuration of the viewpoint detector 6 such as a driver monitoring system (DMS) including an in-vehicle camera. In this example, the viewpoint detector 6 such as a driver monitoring system (DMS) including an in-vehicle camera includes a controller (2) (ECU2) 610 that performs predetermined arithmetic processing by receiving inputs of a signal from a camera (for viewpoint detection) 115 together with signals from the temperature sensor 112 and a steering wheel angle sensor 602. Also, this controller (2) (ECU2) 610 is composed of a vehicle information acquisition unit (2) 611 for receiving inputs of signals from the temperature sensor 112 and the steering wheel angle sensor 602, a camera interface 612 for receiving an input of a signal from the camera (for viewpoint detection) 115, a CPU (2) 613, a nonvolatile memory (2) 614, a volatile memory (2) 615, a communication interface (2) 616, and the like.

A communication unit (2) 617 of the CPU (2) 613 communicates with the communication bus (such as CAN) 300 provided in the vehicle 2 via the communication interface (2) 616, an image analyzer 618 of the CPU (2) 613 performs image analysis by receiving an input of a signal from the camera (for viewpoint detection) 115 via the camera interface 612 by the use of software stored in the nonvolatile memory (2) 614 and the volatile memory (2) 615, and a camera controller 619 of the CPU (2) 613 controls the camera (for viewpoint detection) 115. Namely, the controller (2) (ECU2) 610 constituting the viewpoint detector 6 operates and controls the camera (for viewpoint detection) 115, and simultaneously detects the viewpoint position of the driver based on an image signal from the camera (for viewpoint detection) 115. Note that the detection signal is transmitted to the controller (1) (ECU1) 20 (FIG. 5) of the HUD apparatus 1 described above via the communication interface (2) 616 and the communication bus (such as CAN) 300 provided in the vehicle 2 described above.

Needless to say, the HUD apparatus 1 described above receives information of the viewpoint 5 of the driver from the viewpoint detector 6 such as a driver monitoring system (DMS) including an in-vehicle camera attached to a part of a steering wheel, controls the inclination angle of the concave mirror 52 so as to correspond to the viewpoint position of the driver, and adjusts/controls the position of the virtual image projected on the windshield 3 of the vehicle 2.

Figure 8:
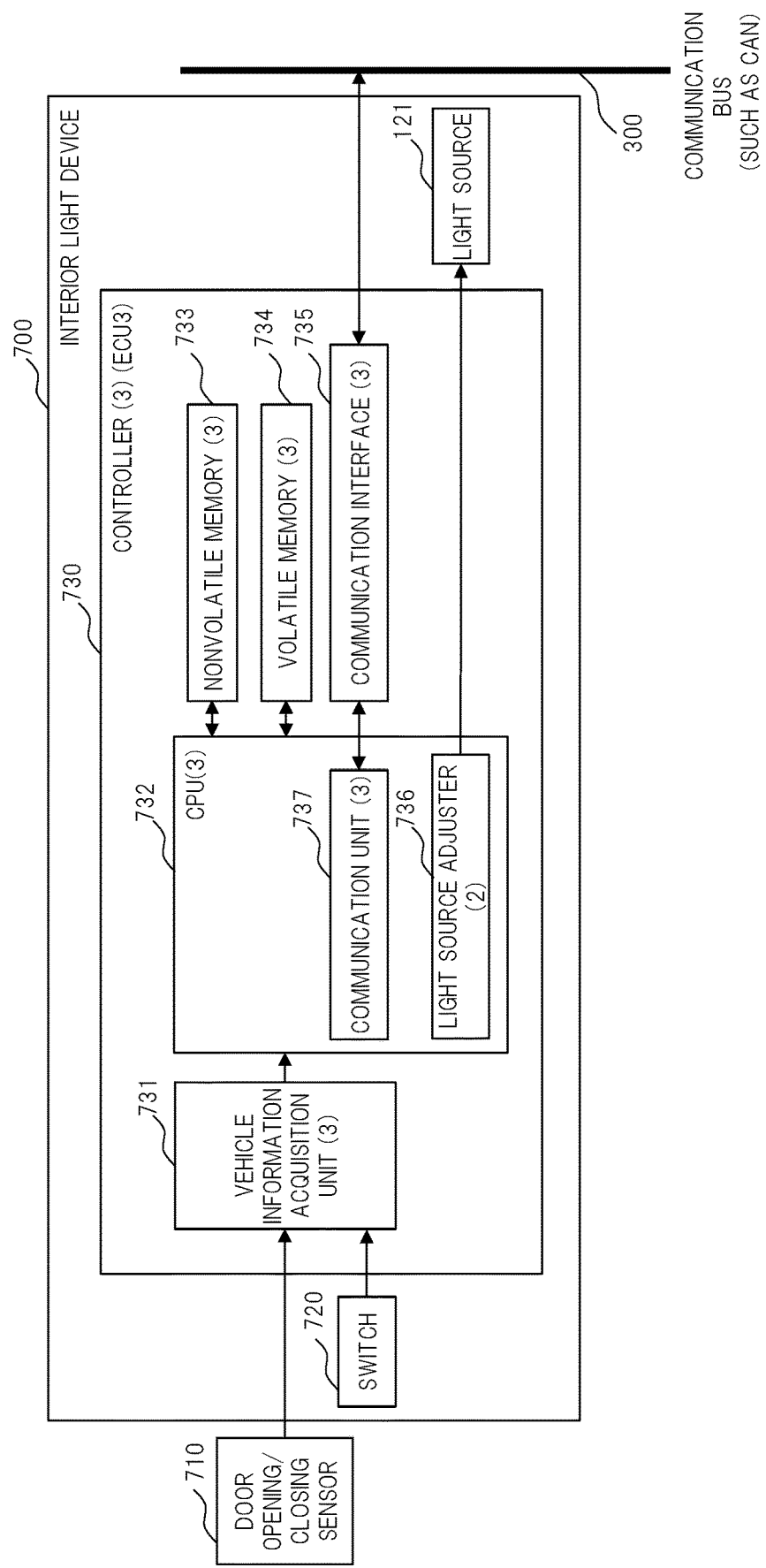
FIG. 8 is a block diagram showing an example of a configuration of an interior light device of the head-up display apparatus.

Further, FIG. 8 shows a block diagram of an interior light device 700 that controls the interior light 120 in the vehicle 2. For example, the interior light device 700 is installed inside the interior light 120. As is clear from FIG. 8, the interior light device 700 receives an input of a signal from a door opening/closing sensor 710 that detects opening/closing of a door in order to turn on/off the interior light in conjunction with opening/closing of the door of the vehicle 2, and includes a switch 720 that turns on/off the interior light independently of the opening/closing of the door and a controller (3) (ECU3) 730 that controls a light source 121 of the interior light 120 (see FIG. 1) based on signals from the sensor and the switch. Further, the controller (3) (ECU3) 730 includes a vehicle information acquisition unit (3) 731 that receives inputs of signals from the door opening/closing sensor 710 and the switch 720, a CPU (3) 732, a nonvolatile memory (3) 733, a volatile memory (3) 734, and a communication interface (3) 735. Also, the CPU (3) 732 is composed of a light source adjuster (2) 736 and the like.

Then, the CPU (3) 732 communicates with the communication bus (such as CAN) 300 provided in the vehicle 2 via the communication interface (3) 735, and the light source adjuster (2) 736 of the CPU (3) 732 determines the state of the light source by the use of software stored in the nonvolatile memory (3) 733 and the volatile memory (3) 734 and controls the light source 121. Namely, the controller (3) (ECU3) 730 of the interior light device 700 turns on/off the light source 121 in the vehicle 2 in response to turning on/off of the switch 720 by the driver in addition to opening/closing of the door. In addition, in this interior light device 700, as will be described in detail below, the CPU (3) 732 constituting the controller (3) (ECU3) 730 monitors the state of the interior light 120, and outputs the state (on/off) as vehicle information to the communication bus (such as CAN) 300 via the communication interface (3) 735 by a communication unit (3) 737.

<Detection of Viewpoint Position of Driver>

Figure 9:
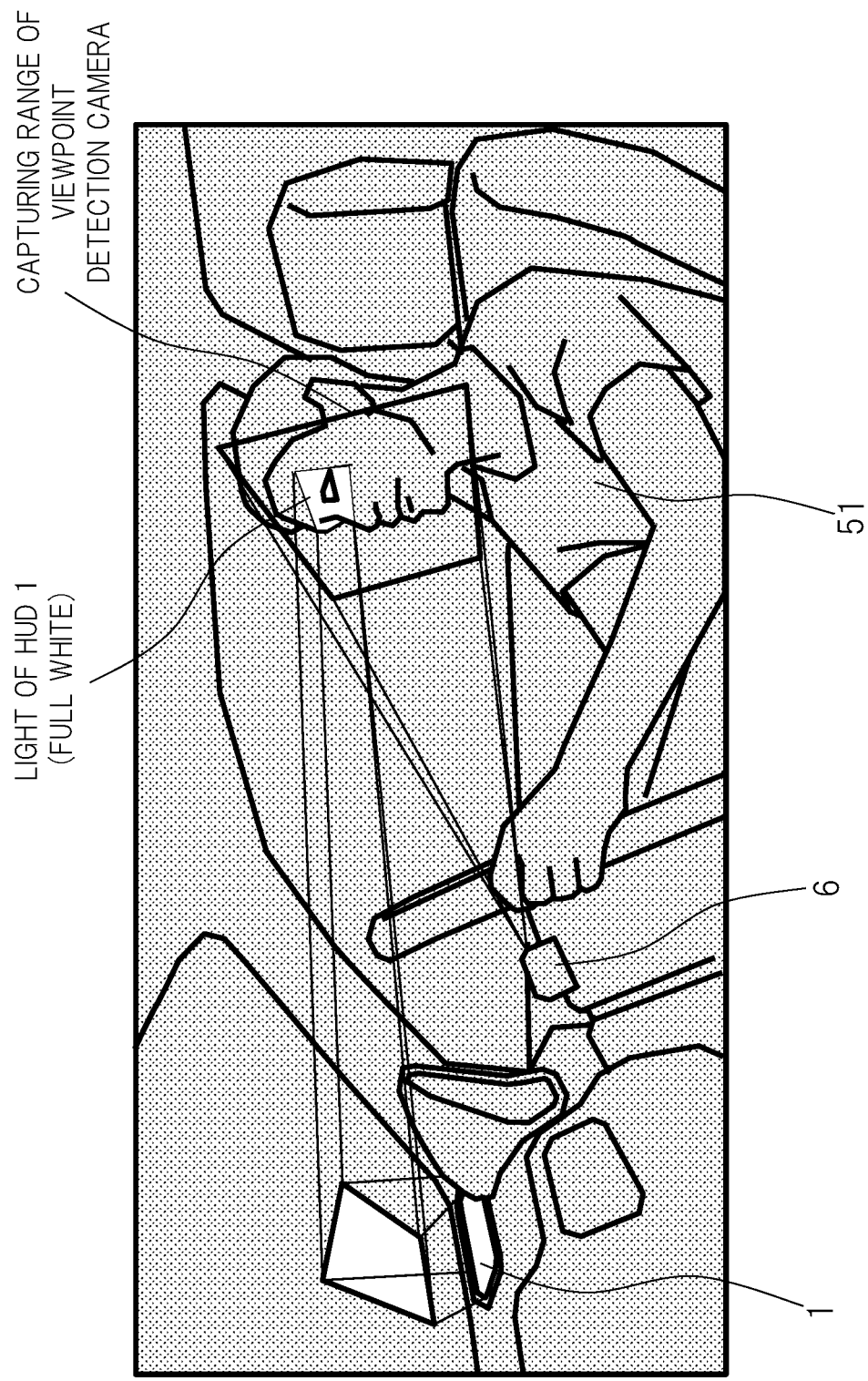
FIG. 9 is an overall configuration diagram for describing detection of a viewpoint position of a driver by the head-up display apparatus.

Next, the detection of the viewpoint position of the driver in the HUD apparatus 1 will be described. Note that, in this embodiment, the viewpoint position of the driver can be detected even at night or in a dark environment such as an indoor parking lot without separately providing a light source such as an infrared LED, that is, by using irradiation light of the image display device 30 which is originally a main element constituting the HUD apparatus 1, and the entire configuration thereof is shown in FIG. 9.

In this embodiment, light from the interior light 120 is used, and as is clear from this figure, white light (full white) is generated by the HUD apparatus 1, and the white light is selectively used as illumination light for detecting the viewpoint position of the driver. Namely, light (image light) from the HUD apparatus 1 that displays a virtual image to the driver is originally directed to a viewpoint of a driver 51, and thus the white light from the HUD apparatus 1 is emitted toward the vicinity centered around the eyes of the driver. Therefore, by using this emitted white light as illumination light, it is possible to detect the viewpoint position of the driver by the viewpoint detector 6 such as a driver monitoring system (DMS) including an in-vehicle camera described above without separately using a light source such as an infrared LED. Consequently, since it is not necessary to additionally provide a light source such as an infrared LED, a more economical apparatus in which an increase in the number of components is suppressed can be realized.

In addition, since white light of the HUD apparatus 1 is emitted as illumination light, as will be described later in detail, it is preferable that the white light be emitted at a timing at which the driver sits on the driver's seat and starts driving (for example, when an engine key is inserted.). Further, the white light can be used not only at night but also in daytime if used in a dark environment (a place such as an indoor parking lot). On the other hand, in a bright environment in the daytime or when the interior light is turned on, the viewpoint position of the driver may be detected by the viewpoint detector 6 such as a driver monitoring system (DMS) including an in-vehicle camera without using the white light of the HUD apparatus 1, and furthermore, the white light of the HUD apparatus 1 may be appropriately turned on as necessary based on a detection signal from the illuminance sensor (see the reference numeral 105 in FIG. 6) provided to detect the brightness outside the vehicle.

In addition, in the actual vehicle 2, the interior light 120 is often turned on/off in conjunction with opening/closing of a door of the vehicle 2 in an environment such as at night, and is turned on as necessary even during driving. Therefore, it is also effective to use the light of the interior light 120 in an on-state as illumination light for detecting the viewpoint position of the driver. Consequently, it is possible to detect the viewpoint position of the driver by using the viewpoint detector 6 such as a driver monitoring system (DMS) including an in-vehicle camera without additionally requiring a dedicated light source such as an infrared LED and without unnecessarily generating white light of the HUD apparatus 1 that may cause the driver to feel dazzled. As described in FIG. 8, the on/off state of the interior light 120 is output to the communication bus (such as CAN) 300 as vehicle information by the controller (3) (ECU3) 730 of the interior light device 700.

<Detection Operation of Viewpoint Position of Driver (Position Adjustment)>

Next, the detection operation of the viewpoint position of the driver (position adjustment) in the HUD apparatus 1 described above will be described in detail below with reference to a flowchart in FIG. 10. Note that, in the HUD apparatus according to the embodiment of the present invention, the HUD apparatus 1 emits white light (full white) (hereinafter, also referred to as "full-white display" or "HUD light") to detect the viewpoint position of the driver, and the direction of the image light for displaying the virtual image with respect to the viewpoint position is adjusted by the mirror driver 42 (see FIG. 3 or 4) based on the detection result. For this reason, basically, it is assumed that the vehicle is not traveling, and the traveling speed of the vehicle from the vehicle speed sensor 101 (see FIG. 6) is monitored. For example, when it is determined that the traveling speed has reached a predetermined value, it is preferable to immediately interrupt the adjustment and perform normal display of the HUD apparatus or not to perform the display by the HUD apparatus.

Figure 10:
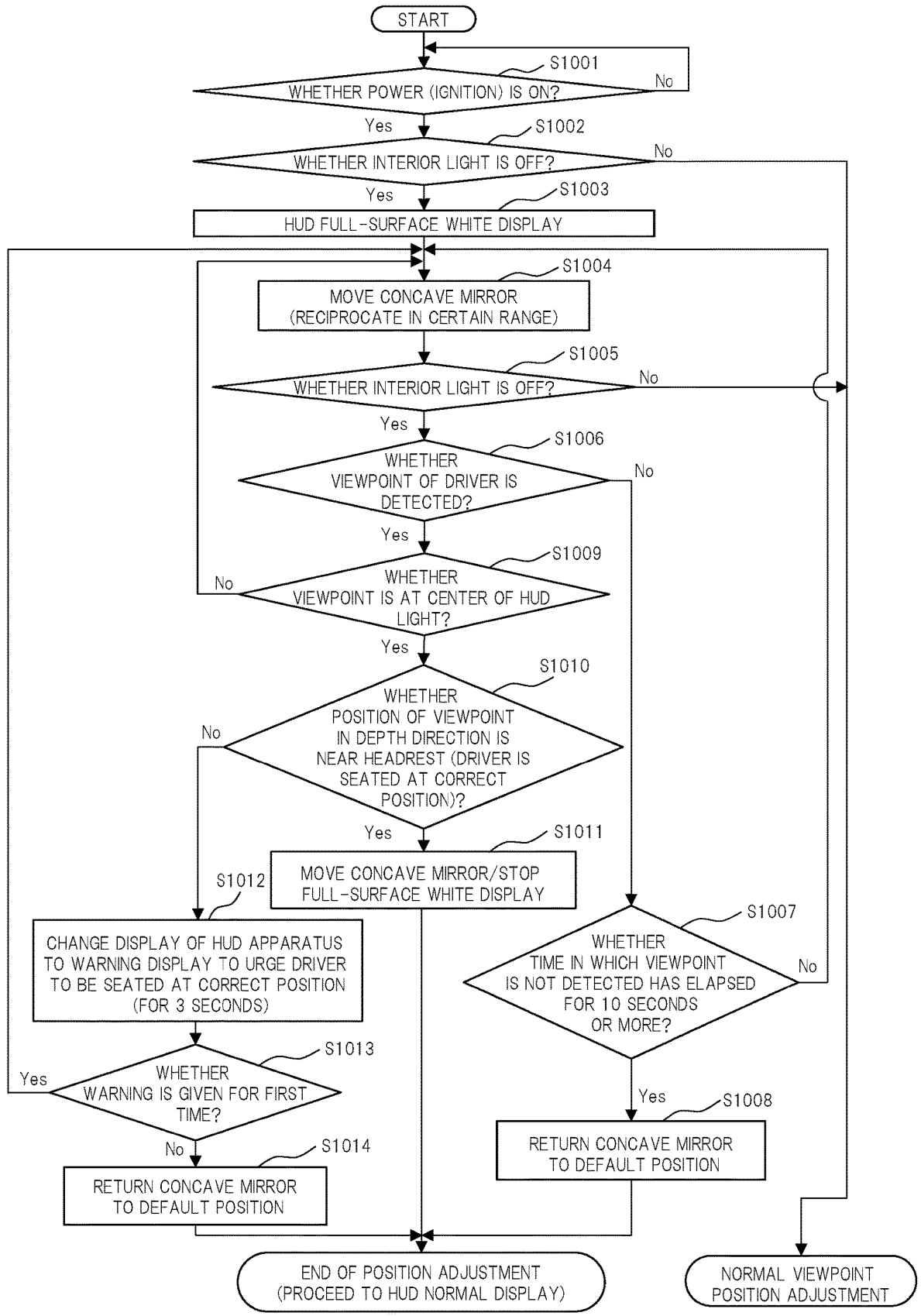
FIG. 10 is a flowchart showing details of a detection operation of a viewpoint position of a driver (position adjustment) in the head-up display apparatus.

First, in FIG. 10, when the detection operation of the viewpoint position of the driver 51 (position adjustment) by the HUD apparatus 1 is started, it is determined whether power (ignition) is turned on in response to, for example, insertion of an engine key in order to confirm that the vehicle is in an activated state (S1001). Subsequently, it is determined whether the interior light 120 is turned off (S1002).

When it is determined as "Yes" as a result of the determination in S1002, the display by the HUD apparatus 1 is set to full-white display (also referred to as "full-surface white display") (S1003). Specifically, by controlling an image signal input to the image display device 30 by the CPU (1) 22 which is an arithmetic processing unit, the HUD light projected from a projector, a liquid crystal display (LCD), or the like is changed to, for example, full-white display light, which is display light having a single color as a whole and a horizontally long rectangular shape, that is, display light corresponding to a lateral width of a face of a human who is the driver. On the other hand, when it is determined as "No" in the determination of S1001, the same determination is repeated again. Further, when it is determined as "No" as a result of the determination in S1002, normal viewpoint position adjustment which will be described in details below is performed under the condition where the interior light 120 is turned on.

Next, in a state of the full-surface white display, the mirror driver 42 (FIG. 5) of the HUD apparatus 1 is driven to rotationally move the concave mirror 52 (S1004). Subsequently, it is determined again whether the interior light 120 is turned off (S1005), and when it is determined as "No" as a result of the determination of S1005, the normal viewpoint position adjustment is performed. However, this rotational movement is continued while making reciprocal movement in a certain range on the face of the driver until the viewpoint of the driver is detected (determined as "Yes") (S1006). Namely, as shown in FIG. 13(a), the full-surface white display from the HUD apparatus 1 is normally set to be performed in the vicinity of eyeballs on the face of the driver 51. Therefore, by making the reciprocal movement of the concave mirror 52 in a certain range, the full-surface white display of the HUD apparatus 1 is moved on the face of the driver 51 as shown in FIG. 13(b) and FIG. 13(c), so that the vicinity of the eyeballs of the driver 51 can be reliably irradiated with the full-surface white display as shown in FIG. 13(d). At this time, it would be preferable to adjust the concave mirror 52 such that the HUD light comes to a center of the eyes (the position of FIG. 13(d)), while confirming the HUD light applied to the driver by the viewpoint detector 6 such as a driver monitoring system (DMS) including an in-vehicle camera.

By this means, it is possible to reliably detect the viewpoint position of the driver 51 by the use of the viewpoint detector 6 such as a driver monitoring system (DMS) including an in-vehicle camera described above. On the other hand, when "No" continues for a predetermined time as a result of the determination as to the detection of the driver's viewpoint in S1006, more specifically, when it is determined whether or not the time in which the viewpoint is not detected has elapsed for 10 seconds or more (S1007) and the result is "No", the process returns to the movement of the HUD mirror (S1004) again. On the other hand, when the result is "Yes", that is, when the detection of the driver fails, the concave mirror 52 is returned to a default position (S1008), and a series of process is ended (end of position adjustment). Then, the process proceeds to the HUD normal display. Note that those skilled in the art will easily understand that the detection of the viewpoint position of the driver by the use of the viewpoint detector 6 such as a driver monitoring system (DMS) including an in-vehicle camera can be realized by extracting an obtained facial image of the driver 51 by image analysis.

Further, when the result of the determination as to the detection of the driver's viewpoint in S1006 is "Yes", in this embodiment, a seating state of the driver 51 in the driver's seat is further detected or determined by image analysis of an image captured by the viewpoint detector 6 such as a driver monitoring system (DMS) including an in-vehicle camera, and the result is displayed. Namely, in this embodiment, first, it is determined whether or not the viewpoint of the driver 51 detected in S1006 is at the center of full-surface white light from the HUD apparatus 1 (S1009). Further, it is determined whether or not the position of the viewpoint of the driver 51 in a depth direction is near the headrest, that is, whether the driver is seated at a correct position (S1010).

Thereafter, when it is determined as "Yes" as a result of the determinations in S1009 and S1010, the movement of the concave mirror 52 is stopped (S1011), and a series of process is ended. At this time, the full-surface white display by the HUD apparatus 1 also simultaneously stops. On the other hand, when it is determined as "No" as a result of the determination in S1009, the process returns to the movement of the HUD mirror (S1004), and further repeats the determination as to whether the interior light is turned off in S1005, the detection of the driver's viewpoint in S1006, and the determination as to whether the viewpoint is at the center of the HUD light in S1009.

Also, when it is determined as "No" as a result of the determination in S1010, this means that the driver 51 is not seated at the correct position, and the display of the HUD apparatus 1 is changed to a warning display to urge the driver to be seated at a correct position such as "Please be seated at the correct position" for a predetermined period such as 3 seconds (S1012). Note that, in this state, even if the warning is displayed by the HUD apparatus 1, there is a high possibility that the warning is not seen. Therefore, in such a case, it would be more effective to perform the warning by audio output by the speaker 60 of FIG. 5, for example, instead of or in addition to the display by the HUD apparatus 1.

Thereafter, it is further determined whether or not the display of the warning in S1012 is the first warning (first time) (S1013), and when it is determined as the first time ("Yes") as a result of the determination in S1013, the process returns to the movement of the concave mirror 52 (S1004) and repeats the steps from S1004. At that time, the warning display is returned to the full-surface white display. On the other hand, when it is determined that the warning is not the first warning (first time) and has already been issued ("No") as a result of the determination in S1013, the position of the driver is regarded as being incorrect, the concave mirror 52 is returned to the default position (S1014), a series of process is ended (end of position adjustment), and then the process proceeds to the HUD normal display.

<Other Embodiments (Illuminance Sensor Control)>

Note that, in the case where the viewpoint position of the driver is detected only by the camera image from the viewpoint detector 6 such as a driver monitoring system (DMS) including an in-vehicle camera as described above, illuminance becomes insufficient particularly at night even when the interior light is turned on, and sufficient accuracy cannot be obtained in some cases. Therefore, it is preferable to determine whether or not the illuminance is sufficient (for example, whether the illuminance is less than 50 lux) based on a signal from the illuminance sensor (105 in FIG. 6) in addition to the viewpoint position of the driver 51, and perform the detection operation of the viewpoint position of the driver based on the result. The details thereof will be described with reference to FIG. 11.

Figure 11:
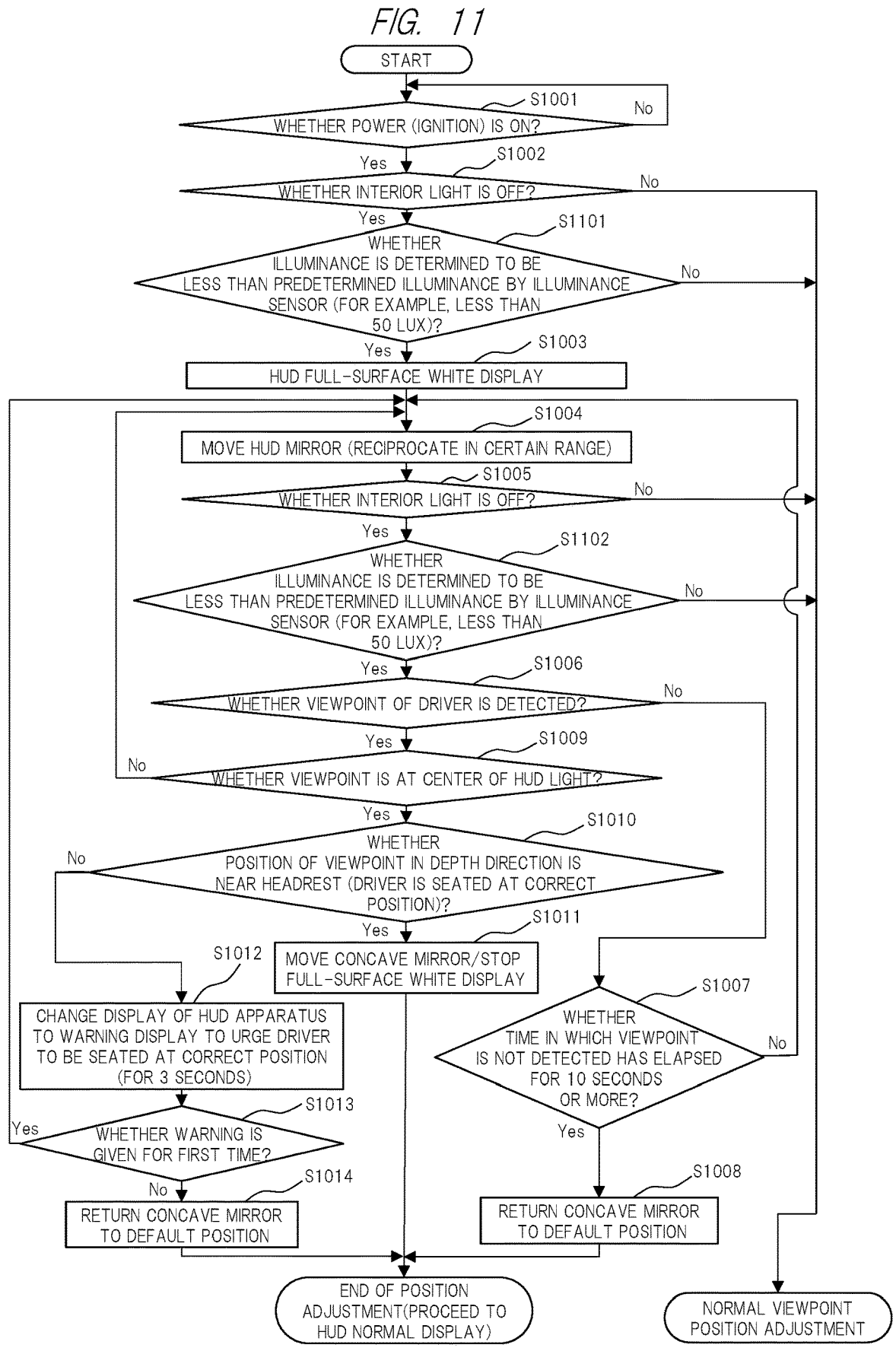
FIG. 11 is a flowchart showing details of the detection operation of a viewpoint position of a driver (position adjustment) in a head-up display apparatus according to another embodiment.

Note that the detection operation of the viewpoint position of the driver (position adjustment) shown in FIG. 11 is basically the same as the operation shown in FIG. 10.

However, it is further determined whether or not the illuminance is less than the predetermined illuminance (for example, less than 50 lux) based on the signal from the illuminance sensor 105 (S1101) following the determination as to whether the interior light is turned off (S1002), and when it is determined as "Yes" as a result of the determination in S1101, the full-surface white display by the HUD apparatus 1 is performed (S1003). On the other hand, when it is determined as "No" as a result of the determination in S1002 or the determination of the illuminance in S1101, the normal viewpoint position adjustment to be described in detail below is performed under the condition where the interior light is turned on.

Further, in the detection operation of the viewpoint position of the driver (position adjustment) shown in FIG. 11, it is determined again whether or not the illuminance is less than predetermined lux (for example, less than 50 lux) based on the signal from the illuminance sensor 105 (S1102) following the subsequent determination as to whether the interior light is turned off (S1005). When it is determined as "Yes" as a result of the determination in S1102, the process proceeds to the detection of the driver's viewpoint in S1006. On the other hand, when it is determined as "No", the process proceeds to the normal viewpoint position adjustment under the condition where the interior light is turned on.

As described above, in the detection operation of the viewpoint position of the driver to which illuminance sensor control is applied according to this embodiment, the determination as to whether the illuminance is sufficient (for example, whether the illuminance is less than 50 lux) is added, so that the viewpoint position of the driver can be detected with sufficient accuracy by the full-white display by the HUD apparatus 1 even when the interior light is turned on at night but the illuminance thereof is insufficient.

<Normal Viewpoint Position Adjustment>

Next, the process which is executed when it is determined as "No" as a result of the determination as to whether the interior light is turned off in the flow of FIG. 10 (S1002 and S1005) and when it is determined as "No" as a result of the determination of the illuminance in the flow of FIG. 11 (S1101 and S1102), that is, the normal viewpoint position adjustment will be described below.

Figure 12:
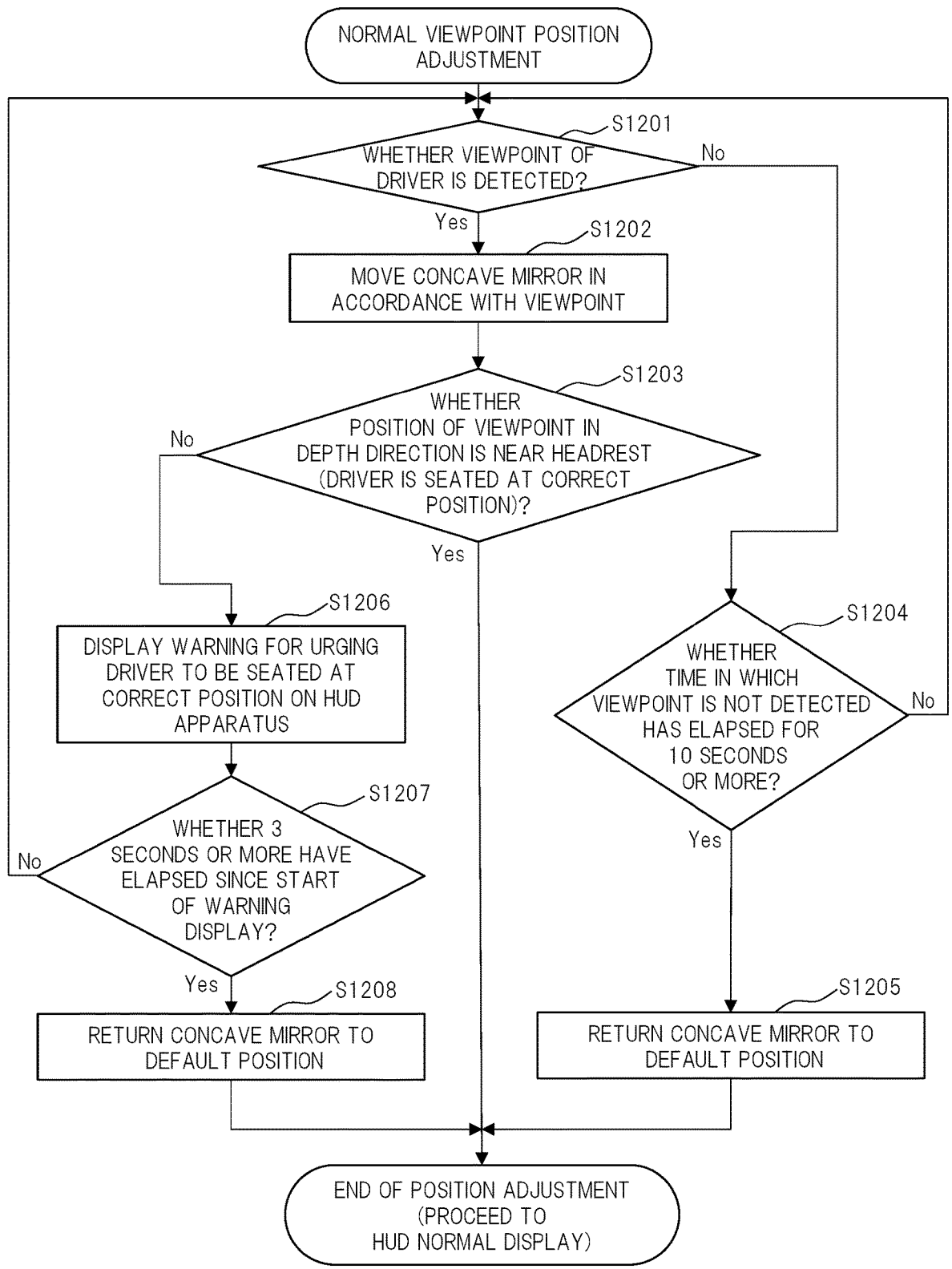
FIG. 12 is a flowchart showing details of normal viewpoint position adjustment in FIG. 10 and FIG. 11.

FIG. 12 is a flowchart showing an example of a procedure of the normal viewpoint position adjustment. As is clear from the figure, when the normal viewpoint position adjustment is started, it is determined whether or not the viewpoint of the driver is detected (S1201). When it is determined as "Yes" as a result of the determination in S1201, the concave mirror 52 is moved in accordance with the detected viewpoint of the driver (S1202). Thereafter, it is determined whether or not the position of the viewpoint of the driver 51 in the depth direction is near the headrest, that is, whether the driver is seated at the correct position (S1203), and when it is determined as "Yes" as a result of the determination in S1203, a series of position adjustment is ended and the process proceeds to the HUD normal display.

On the other hand, when it is determined as "No" as a result of the determination in S1201, it is determined whether or not the time in which the viewpoint is not detected has elapsed for a predetermined time (for example, 10 seconds or more) (S1204), and when it is determined as "Yes" as a result of the determination in S1204, the concave mirror 52 is returned to the default position (S1205), and then a series of position adjustment is ended and the process proceeds to the HUD normal display. On the other hand, when it is determined as "No" as a result of the determination in S1204, the process returns to S1201, and the process in and after S1201 is repeated.

Further, when it is determined as "No" as a result of the determination in S1203, since the driver 51 is not seated at the correct position, the display of the HUD apparatus 1 is changed to a warning display for urging the driver 51 to be seated at the correct position (S1206). Thereafter, it is determined whether or not a predetermined period (for example, 3 seconds or more) has elapsed from the start of the warning display (S1207), and when it is determined as "Yes" as a result of the determination in S1207, the concave mirror 52 is returned to the default position (S1208), a series of process (position adjustment) is ended, and the process proceeds to the normal display of the HUD apparatus 1. On the other hand, when it is determined that the predetermined period (for example, 3 seconds or more) has not elapsed, that is, determined as "No" as a result of the determination in S1207, the process returns to the viewpoint detection determination process (S1201) to execute a series of process again.

Note that, in the above description, the HUD light generated by the HUD apparatus 1 for performing the detection operation of the viewpoint position of the driver (position adjustment) has been described as white light (full white), and this is selected in order to more accurately measure the distance from the viewpoint detector 6 such as a driver monitoring system (DMS) including an in-vehicle camera to the viewpoint of the driver. However, the present invention is not limited thereto, and it is also possible to adopt entire single color light of another color such as yellowish green which is gentle to the human eyes instead of the white light. Furthermore, in consideration of an analysis (for example, analysis of the amount of movement) of an image from the viewpoint detector 6 such as a driver monitoring system (DMS) including an in-vehicle camera, grid display with a lattice shape crossing vertically and horizontally in the rectangular light may be added in the HUD light instead of the light having a single color as a whole and a horizontally long rectangular shape.

As described above in detail, in the HUD apparatus 1 according to the embodiment of the present invention, the detection of the viewpoint position of the driver by the viewpoint detector 6 such as a driver monitoring system (DMS) including an in-vehicle camera operated with normal visible light is possible by selectively using the existing interior light provided in the vehicle 2 or the light source of the HUD apparatus 1 without requiring a dedicated light source or the like for detecting the viewpoint position of the driver even in a situation where sufficient external light like in daytime cannot be obtained. More specifically, the on/off state of the interior light is monitored as vehicle information of a communication bus such as a CAN provided in the vehicle, and light from the interior light is used when the interior light is turned on and white light (full white) from the HUD apparatus 1 is used when the interior light is turned off. By this means, it is possible to use the viewpoint detector 6 or the like such as a driver monitoring system (DMS) including an in-vehicle camera that is normally mounted in the apparatus and is operated with visible light to confirm the position of the driver, and it is possible to reliably detect a viewpoint position of the driver who is the observer of the virtual projection image without unnecessarily generating white light by the HUD apparatus 1 that may cause visual glare. Namely, a head-up display apparatus which is excellent in practical use and economical efficiency and capable of suitably and reliably detecting a viewpoint position of a driver and controlling a position of a virtual projection image is realized.

In the foregoing, the invention made by the inventors of this application has been specifically described based on the embodiments, but the present invention is not limited to the embodiments described above and can be variously modified within the range not departing from the gist thereof. For example, the embodiments above have been described in detail in order to make the present invention easily understood, and the present invention is not necessarily limited to the embodiments having all of the described configurations. Also, a part of the configuration of one embodiment may be replaced with the configuration of another embodiment, and the configuration of one embodiment may be added to the configuration of another embodiment. Furthermore, another configuration may be added to a part of the configuration of each embodiment, and a part of the configuration of each embodiment may be eliminated or replaced with another configuration.

INDUSTRIAL APPLICABILITY

The present invention is applicable to a head-up display apparatus that projects an image on a transparent glass plate or the like.

REFERENCE SIGNS LIST

1 HUD apparatus
2 vehicle
3 windshield
4 vehicle information
5 driver (viewpoint)
6 viewpoint detector
20 controller (1)
21 vehicle information acquisition unit (1)
22 CPU (1)
23 nonvolatile memory (1)
24 volatile memory (1)
30 image display device
31 backlight (light source)
42 mirror driver
60 speaker
115 camera (for viewpoint detection)
120 interior light
300 communication bus (such as CAN)
700 interior light device

The invention claimed is:

1. A head-up display apparatus configured to project an image on a windshield of a transportation to display a virtual image based on the image to a driver, the head-up display apparatus comprising:
an image display including a light source and a display element configured to form the image;
an image projector configured to project and reflect image light emitted from the image display onto the windshield to display the virtual image in front of the transportation; and
a driving element configured to move a position of the virtual image projected by the image projector based on information of a viewpoint of the driver detected by a driver's viewpoint detector mounted in the transportation,
wherein, when it is determined that the transportation is not traveling or a traveling speed of the transportation does not reach a predetermined value, the driver's viewpoint detector detects the viewpoint of the driver by using light of an interior light device mounted in the transportation as illumination light or by irradiating a face of the driver with light of the light source of the image display as illumination light without using a dedicated light source,
and
wherein, when illuminance based on a signal from an illuminance sensor is less than a predetermined illuminance, the viewpoint of the driver is detected by using the light of the light source of the image display as the illumination light.

2. The head-up display apparatus according to claim 1, wherein, when it is determined that the transportation is not traveling or the traveling speed of the transportation does not reach the predetermined value and further viewpoint detection by the driver's viewpoint detector cannot be performed only by external light of the transportation, the driver's viewpoint detector detects the viewpoint of the driver by using light of the interior light device mounted in the transportation or light of the light source of the image display as illumination light without using the dedicated light source.

3. The head-up display apparatus according to claim 1, wherein the face of the driver is irradiated with the light of the light source of the image display as illumination light when the interior light device is turned off.

4. The head-up display apparatus according to claim 1, wherein a state of the interior light device is output to a communication unit provided in the head-up display apparatus.

5. The head-up display apparatus according to claim 4, wherein the driver's viewpoint detector obtains the state of the interior light device via the communication unit.

6. The head-up display apparatus according to claim 1, wherein the illumination light from the light source of the image display is composed of light of a single color as a whole.

7. The head-up display apparatus according to claim 6, wherein the illumination light from the light source of the image display is white light.

8. The head-up display apparatus according to claim 6, wherein the illumination light from the light source of the image display is rectangular light having a lateral width corresponding to a lateral width of the face of the driver.

9. The head-up display apparatus according to claim 6, wherein the illumination light from the light source of the image display is vertically moved along the face of the driver by moving the image projector by the driving element.

10. The head-up display apparatus according to claim 1, wherein the driver's viewpoint detector detects the viewpoint of the driver without using infrared rays from said dedicated light source.

11. The head-up display apparatus according to claim 1, wherein, when it is determined that the signal from the illuminance sensor is more than predetermined illuminance, the viewpoint of the driver is detected by using the light of the interior light device as the illumination light when the interior light device is turned on.

* * * * *